US007223606B2

(12) United States Patent
Nedospasov et al.

(10) Patent No.: US 7,223,606 B2
(45) Date of Patent: May 29, 2007

(54) METHODS OF DETECTING NITROTYROSINE AND AMINOTYROSINE RESIDUES OF PEPTIDES AND PROTEINS

(75) Inventors: Andrei Nedospasov, Moscow (RU); Nataliya Beda, Moscow (RU); Tatiana Pimenova, Moscow (RU); Emil Martin, Houston, TX (US); Ferid Murad, Houston, TX (US)

(73) Assignee: Board of Regents of the University of Texas System, Austin, TX (US)

( * ) Notice: Subject to any disclaimer, the term of this patent is extended or adjusted under 35 U.S.C. 154(b) by 0 days.

(21) Appl. No.: 11/147,552

(22) Filed: Jun. 8, 2005

(65) Prior Publication Data

US 2006/0035385 A1    Feb. 16, 2006

Related U.S. Application Data

(60) Provisional application No. 60/579,041, filed on Jun. 11, 2004.

(51) Int. Cl.
*G01N 33/00* (2006.01)
(52) U.S. Cl. .......................... 436/106; 436/63; 436/86; 436/110; 436/164; 436/166; 435/6
(58) Field of Classification Search .................... 436/8, 436/63, 64, 86, 106, 110, 116, 164, 166; 435/6
See application file for complete search history.

(56) References Cited

U.S. PATENT DOCUMENTS

| 4,315,756 | A * | 2/1982 | Zeidler et al. | ................. 44/328 |
| 2002/0022244 | A1 * | 2/2002 | Kim et al. | ..................... 435/25 |
| 2003/0165983 | A1 * | 9/2003 | Gibson et al. | ............... 435/7.1 |

FOREIGN PATENT DOCUMENTS

SU            935506      *    6/1982

OTHER PUBLICATIONS

Zhedek et al. Abstract from Zhurnal Prikladnoi Khimii, vol. 25, 1952, pp. 441-449.*
Rodionov. Abstract from Kozhevenno-Obuvnaya Promyshlennost SSSR, No. 7, 1959, pp. 18-20.*
Akaike, T., et al., "8-Nitroguanosine formation in viral pneumonia and its implication for pathogenesis," PNAS, vol. 100, No. 2, p. 685-690 (Jan. 21, 2003).
Alvarez, B., et al., "Peroxynitrite-Dependent Tryptophan Nitration," Chem. Res. Toxicol., vol. 9, No. 2, p. 390-396 (1996).
Andreadis, A.A., et al., "Oxidative and Nitrosative Events in Asthma," Free Radical Biology & Medicine, vol. 35, No. 3, p. 213-225 (2003).
Baldus, S., et al., "Endothelial transcytosis of myeloperoxidase confers specificity to vascular ECM proteins as targets of tyrosine nitration," The Journal of Clinical Investigation, vol. 108, No. 12, p. 1759-1770 (Dec. 2001).

Beda, N.V., et al., "Micellar catalysis for oxidation of nitrix oxide (NO) in the multi-phase systems in vivo," FEBS Letters, vol. 453, p. 229-235 (1999).
Bian, K., et al., "The nature of heme/iron-induced protein tyrosine nitration," PNAS, vol. 100, No. 10, p. 5712-5717 (May 13, 2003).
Chen, H.J.C., et al., "Lipoyl dehydrogenase catalyzes reduction of nitrated DNA and protein adducts using dihydrolipoic acid or ubiquinol as the cofactor," Chemico-Biological Interactions, vol. 140, p. 199-213 (2002).
Dawson, T.M., et al., "Molecular Pathways of Neurodegeneration in Parkinson's Disease," Science, vol. 302, p. 819-822 (Oct. 31, 2003).
Ehsan, A., et al., "Nitric Oxide Pathways Human Bladder Carcinoma," Cancer, vol. 95, No. 11, p. 2293-2301 (Dec. 1, 2002).
Gaut, J.P., et al., "Myeloperoxidase produced nitrating oxidants in vivo," The Journal of Clinical Investigation, vol. 109, No. 10, p. 1311-1319 (May 2002).
Giasson, B.I., et al., "Oxidative Damage Linked to Neurodegeneration by Selective a-Synuclein Nitration in Synucleinopathy Lesions," Science, vol. 290, p. 985-989 (Nov. 3, 2000).
Goldstein, S., et al., "Tyrosine Nitration by Simultaneous Generation of NO and O2 under Physiological Conditions," The Journal of Biological Chemistry, vol. 275, No. 5, p. 3031-3036 (Feb. 4, 2000).
Gordin, V.A., et al., "NO catastrophes in vivo as a result of micellar catalysis," FEBS Letters, vol. 424, p. 239-242 (1998).
Herrero, M.B., et al., "Tyrosine nitration in human spermatozoa: a physiological function of peroxynitrite, the reaction product of nitric oxide and superoxide," Molecular Human Reproduction, vol. 7, No. 10, p. 913-921 (2001).
Irie, Y., et al., "Histone H1.2 is a substrate for denitrase, an activity that reduces nitrotyrosine i mmunoreactivity in proteins," PNAS, vol. 100, No. 10, p. 5634-5639 (May 13, 2003).
Kamisaki, Y., et al., "An activity in rat tissues that modifies nitrotyrosine-containing proteins," Proc. Natl. Acad. Sci., vol. 95, p. 11584-11589 (Sep. 1998).

(Continued)

*Primary Examiner*—Maureen M. Wallenhorst
(74) *Attorney, Agent, or Firm*—Conley Rose, P.C.

(57) ABSTRACT

Methods and compositions are disclosed for quantifying and/or identifying a nitroderivative compound, or a residue thereof, and are applicable for assessing in vivo nitrative stress and for aiding in diagnosis of mammalian pathologies such as asthma, atherosclerosis, Alzheimer's disease, inflammation, ischemia, Parkinson's disease, and cancer. A preferred method comprises a) providing a sample containing the nitroderivative compound, or residue thereof, in the form of a diazo compound or residue thereof; b) azo-coupling the diazo compound, or residue thereof, to a target compound capable of producing a signal, to yield an azo-coupled compound; c) isolating the nitroderivative compound, or residue thereof, or the azo-coupled compound; d) quantitating and/or detecting the signal, to yield a quantitation and/or detection result; and e) determining from the quantitation and/or detection result the identity and/or concentration of the nitroderivative compound, or residue thereof, in the sample.

26 Claims, 6 Drawing Sheets

OTHER PUBLICATIONS

Kuo, W.N., et al., "Nitration/S-nitrosation of proteins by peroxynitrite-treatment and subsequent modification by glutathione S-transferase and glutathione peroxidase," Molecular and Cellular Biochemistry, vol. 233, p. 57-63 (2002).

Kuo, W.N., et al., "Denitration of peroxynitrite-treated proteins by 'protein nitratases' from rat brain and heart," Molecular and Cellular Biochemistry, vol. 201, p. 11-16 (1999).

Miyagi, M., et al., "Evidence that Light Modulates Protein Nitration in Rat Retina," Molecular & Cellular Proteomics, vol. 1, No. 4, p. 293-303 (2002).

Nikov, G., et al., "Analysis of nitrated proteins by nitrotyrosine-specific affinity probes and mass spectrometry," Analytical Biochemistry vol. 320, p. 214-222 (2003).

Petersson, A.S., et al., "Investigation of tyrosine nitration in proteins by mass spectrometry," Journal of Mass Spectrometry, vol. 36, p. 616-625 (2001).

Reiter, C.D., et al., "Superoxide Reacts with Nitric Oxide to Nitrate Tyrosine at Physiological pH via Peroxynitrite," The Journal of Biological Chemistry, vol. 275, No. 42, p. 32460-32466 (Oct. 20, 2000).

Sarver, A., et al., "Analysis of Peptides and Proteins Containing Nitrotyrosine by Matrix-Assisted Laser Desorption/Ionization Mass Spectrometry," J. Am. Soc. Mass. Spectrom. vol. 12, 439-448 (2001.

Tomohiro, S., et al., "Tyrosine Nitration by Peroxynitrite Formed from Nitric Oxide and Superoxide Generated by Xanthine Oxidase," The Journal of Biological Chemistry, vol. 275, No. 42, p. 32467-32474 (Oct. 20, 2000).

Shafirovich, V., et al., "Photochemically Catalyzed Generation of Site-Specific 8-Nitroquanine Adducts in DNA by the Reaction of Long-Lived Neutral Guanine Radicals with Nitrogen Dioxide," Chem. Res. Toxicol., vol. 15, p. 591-597 (2002).

Shishehbor, M.H., et al., "Association of Nitrotyrosine Levels with Cardiovascular Disease and Modulation by Statin Therapy," JAMA, vol. 289, No. 13, p. 1675-1680 (Apr. 2, 2003).

Sodum, R.S., et al., "Amination of Tyrosine in Liver Cytosol Protein of Male F344 Rats Treated with 2-Nitropropane, 2-Nitrobutane, 3-Nitropentane, or Acetoxime," Chem. Res. Toxicol., vol. 10, p. 1420-1426 (1997).

Thomas, D.D., et al., "Protein nitration if mediated by heme and free metals through Fenton-type chemistry: an alternative to the NO/O2 reaction," PNAS, vol. 99, No. 20, p. 12691-12696 (Oct. 1, 2002).

Turko, I.V., et al., "Protein Nitration in Cardiovascular Diseases," Pharmacological Reviews, vol. 54, No. 4, p. 619-634 (2002).

Van Der Vliet, A., et al., "Formation of Reactive Nitrogen Species during Peroxidase-catalyzed Oxidation of Nitrite," The Journal of Biological Chemistry, vol. 272, No. 12, p. 7617-7625 (Mar. 21, 1997).

Van Der Vliet, et al., "Tyrosine Modification by Reactive Nitrogen Species: A Closer Look," Archives of Biochemistry and Biophysics, vol. 319, No. 2, p. 341-349 (Jun. 1, 1995).

Wu, W., et al., "Eosinophil Peroxidase Nitrates Protein Tyrosyl Residues," The Journal of Biological Chemistry, vol. 274, No. 36, p. 25933-25944 (Sep. 3, 1999).

Zhang, H., et al., "Transmembrane Nitration of Hydrophobic Tyrosyl Peptides," The Journal of Biological Chemistry, vol. 278, No. 11, p. 8969-8978 (Mar. 14, 2003).

Zhang, H., et al., "Bicarbonate Enhances the Hydroxylation, Nitration, and Peroxidation Reactions Catalyzed by Copper, Zinc Superoxide Dismutase," The Journal of Biological Chemistry, vol. 275, No. 19, p. 14038-14045 (May 12, 2000).

* cited by examiner

METHODS OF DETECTING NITROTYROSINE AND AMINOTYROSINE RESIDUES OF PEPTIDES AND PROTEINS

CROSS-REFERENCE TO RELATED APPLICATIONS

This application claims the benefit under 35 U.S.C. § 119(e) of U.S. Provisional Patent Application No. 60/579,041 filed Jun. 11, 2004, the disclosure of which is hereby incorporated herein by reference.

STATEMENT REGARDING FEDERALLY SPONSORED RESEARCH OR DEVELOPMENT

This invention was made in whole or in part with funding from the National Institutes of Health (Grant No. HL064221) Accordingly, die United States Government has certain rights in this invention.

BACKGROUND OF THE INVENTION

1. Field of the Invention

The present invention generally relates to nitroderivative compounds such as diazo compounds, and residues thereof (e.g., diazotyrosine-containing proteins). More particularly, the invention relates to such compounds azo-coupled to a signal-producing target compound, and to methods and compositions for identifying or quantifying such compounds, especially in biological specimens. Still more particularly, the invention relates to assessing in vivo nitrative stress, and to aiding in the detection of illness or disease by quantitating or detecting the signal resulting from such azo-coupling.

2. Description of Related Art

The nitration of tyrosine residues in proteins to form 3-nitrotyrosine has been characterized as one of several nitric oxide dependent chemical modifications of proteins. Nitrogen dioxide and derivatives of peroxynitrite (both are products of the non-enzymatic oxidation of nitric oxide in vivo) [1–8], reactive compounds produced from nitrite by peroxidases and other enzymes with metal cofactors, as well as by non-enzymatic Fenton-type reactions [9–14] are main natural protein nitration agents. In addition, it was also shown that intense visible light elevates tyrosine nitration in retina, although the chemistry of this process remains poorly understood [15]. Nitrotyrosine levels increase dramatically when the cells are experiencing nitrosative or oxidative stress, and is associated with inflammation, asthma and atherosclerosis [16, 17]. Nitration of specific residues in proteins may play a role in regulating Alzheimer's and Parkinson disease, and cancer [18–21]. The presence of nitrotyrosine residues in proteins can change their activity and/or half-life and may have physiological effects in the normal conditions. For example, tyrosine nitration of sperm proteins occurs in capacitated human spermatozoa [22]. It was shown that nitrotyrosine residues can lead to other processes of protein modifications [23–25]. One of them is the reduction of nitrotyrosine to aminotyrosine, probably through the nitroso- and hydroxyamino derivatives. This reduction can be both enzymatic and non-enzymatic [26, 27] and is regulated independently on nitration mechanism. Thus, at every moment the cell, organ or organism has a unique composition and pattern of nitro- and aminotyrosine containing proteins.

Formation of aminotyrosine can be attributed to several alternative pathways. Sodum and Fiala found high levels of aminotyrosine (>0.1% of the total protein tyrosine) in the liver of rats treated with 2-nitropropane, a strong hepato-carcinogen, or few other secondary nitroalkanes, oximes as well as hydroxylamine-O-sulfonate [28]. Determination and quantification of these NO-dependent modifications of proteins are necessary to understand the key cellular processes and could have clinical applications [29].

SUMMARY OF THE INVENTION

It is now proposed that aminotyrosine residues can be diazotized in vivo yielding diazotyrosine-containing proteins, and it is demonstrated herein that diazotyrosine residues in peptides and proteins have significant stability and can be identified as products of azo-coupling with naphthylamine derivatives.

In accordance with certain embodiments of the present invention, a method of quantifying and/or identifying a nitroderivative compound, or residue thereof, is provided. The method generally comprises (a) providing a sample containing the nitroderivative compound, or a residue thereof, in the form of a diazo compound or a residue of the diazo compound; (b) azo-coupling the diazo compound, or its residue, to a target compound capable of producing a signal, to yield an azo-coupled complex; (c) quantitating and/or detecting the signal, to yield a quantitation and/or detection result; and (d) determining from that quantitation and/or detection result the identity and/or concentration of the nitroderivative compound, or residue thereof, in the sample. In certain embodiments, the method includes isolating the nitroderivative compound, or residue thereof, or the azo-coupled complex. In certain embodiments of the method, the nitroderivative compound, or residue thereof, is a component of a protein, peptide or nucleic acid. For example, the nitroderivative compound, or residue thereof, may be chosen from the group consisting of nitrotyrosine, aminotyrosine, and diazotyrosine, and residues thereof, in some embodiments.

In certain embodiments of the method, the nitroderivative compound, or residue thereof, is chosen from the group consisting of tyrosine, trypthophan, histidine, and guanosine.

In certain embodiments of an above-described method, step (a) includes converting the nitroderivative compound, or residue thereof, to a diazo compound, or residue thereof. For instance, step (a) may include reducing the nitroderivative compound, or a residue thereof, prior to converting the nitroderivative compound, or residue thereof, to a diazo compound, or residue thereof. In some embodiments, the nitroderivative compound is nitrotyrosine and step (a) comprises reducing the nitrotyrosine, or residue thereof, to an aminotyrosine compound, or residue thereof.

In certain embodiments of the method, step (c) comprises spectral or colorimetric monitoring of an azo-coupling reaction. In certain embodiments of the method, the sample comprises a biological sample containing at least one nitroderivative compound, or residue thereof.

In certain embodiments of an above-described method, the target compound of the azo-coupling step comprises a synthetic molecule. For instance, the synthetic target molecule contains a naphthyl moiety in some embodiments.

Also provided in accordance with certain embodiments of the present invention is a method of detecting illness or disease in a mammalian subject. This detection method generally comprises (a) carrying out an above-described quantitating/detecting method wherein the sample of interest is a biological sample from a subject in need of such testing; and (b) determining from the identification and/or concentration of said nitroderivative compound, or residue thereof, in the biological sample, the presence and/or level of illness or disease in the subject.

The present invention also provides, in certain embodiments, a method to aid in diagnosing in a mammalian subject a pathology associated with a nitroderivative compound. This diagnostic method generally comprises carrying out an above-described method of detecting illness or disease, and then determining from the presence and/or level of nitroderivative compound in the biological sample a diagnosis as to the pathology in the subject. For example, a diagnosis as to such pathologies as asthma, atherosclerosis, inflammation, ischemia, Alzheimer's disease, Parkinson's disease and cancer is determined.

Further provided in accordance with certain embodiments of the present invention is a method of assessing in vivo nitrative stress in a subject. This method generally comprises (a) providing a biological specimen from the subject, the specimen comprising a protein or peptide containing a nitro-modified amino acid residue chosen from the group consisting of nitrotyrosine, aminotyrosine, diazotyrosine, and diazoaminotyrosine; (b) reducing the nitrotyrosine and/or diazotyrosine residue(s), if present, to form, respectively, aminotyrosine and/or diazoaminotyrosine residue(s); (c) converting the nitrotyrosine and/or diazotyrosine residue(s), if present, to form, respectively, diazotyrosine and/or diazoaminotyrosine residue(s); (d) coupling the diazotyrosine and/or diazoaminotyrosine residue(s) to a target compound capable of producing a signal, such that an azo-coupled protein or peptide complex is provided; (e) isolating the protein or peptide, or the azo-coupled protein or peptide complex; (f) quantitating and/or detecting the signal, to yield a quantitation and/or detection result; (g) determining from the quantitation and/or detection result the identity and/or concentration of the nitrotyrosine or nitroaminotyrosine residue(s) in the biological specimen; and (h) determining from the identification and/or concentration of the nitrotyrosine or nitroaminotyrosine residue(s) a level of nitrative stress in the subject.

Still further provided in accordance with certain embodiments of the present invention, is a composition comprising a diazo compound, or residue thereof, azo-coupled to a target compound capable of producing a quantifiable and/or detectable signal. In some embodiments, the diazo compound residue is a component of a protein, peptide or nucleic acid azo-coupled with a target molecule capable of producing a quantifiable and/or detectable signal. In some embodiments, the diazo compound residue comprises a diazonitrotyrosine or diazoaminotyrosine residue in a protein or peptide. In some embodiments, the composition comprises an isolated complex containing a protein, peptide or nucleic acid azo-coupled to said target compound. For example, the target compound could comprise a naphthyl group. These and other embodiments, features and advantages of the present invention will become apparent with reference to the following description and drawings.

BRIEF DESCRIPTION OF THE DRAWINGS

FIG. 1A depicts Scheme 1. FIG. 1B depicts Scheme 2.

In FIG. 2A squares indicate the effects of nitrosation time on the yield of BSA-NEDA at 0°. Triangles indicate the stability of diazo-BSA after the removal of nitrites was monitored by varying the incubation times with sulfamate at 37° C. before addition of BSA-NEDA. FIG. 2B shows the effect of urea on the efficiency of nitrosation. FIG. 2C shows the effect of NEDA concentration on the efficiency of azo-coupling.

FIG. 5A: Coomassie stained. FIG. 5B: Western blot.

DETAILED DESCRIPTION OF THE PREFERRED EMBODIMENTS

Figure 1A:
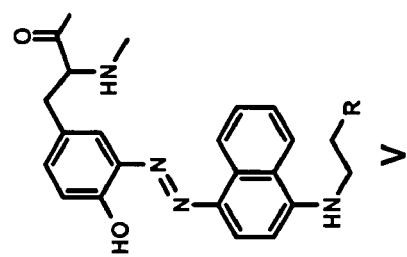
FIGS. 1A–B are schema showing the chemical structures of starting compounds, intermediates, and reaction products in accordance with certain embodiments of the present invention.
Figure 1A:
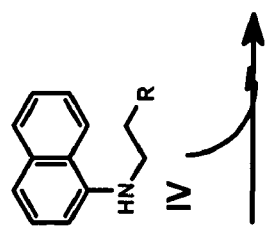
Figure 1A:
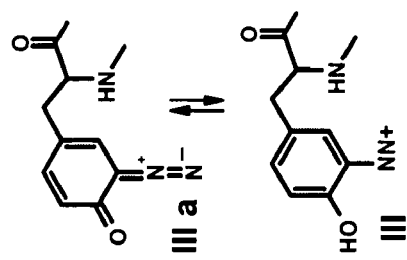
Figure 1A:
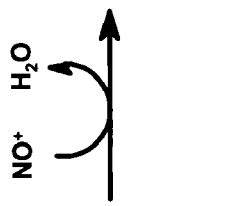
Figure 1A:
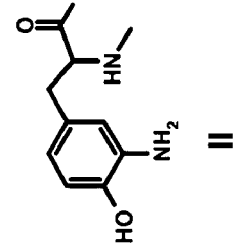
Figure 1A:
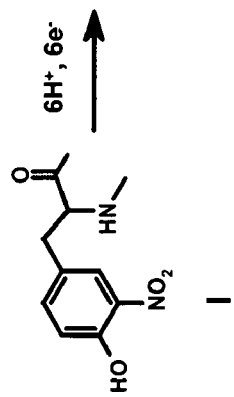

It is disclosed herein for the first time that nitrotyrosine residues in peptides and proteins, as well as its reduced form, can be converted to diazotyrosine derivatives. These diazo compounds have unique chemical reactivity allowing azo-coupling of diazotyrosine-containing proteins with synthetic targets. These properties can be used to identify and quantify protein nitration and/or other nitroderivatives of proteins. Moreover, because nitrosation is a common chemical reaction for all nitric oxide produced organisms and its efficiency for proteins is elevated due to micellar catalysis (micellar oxidative nitrosation) [30–32], diazotization of aminotyrosine residues of proteins may be a natural process of diazotyrosine formation in vivo.

Nitration of tyrosine residues is known as one of several nitric oxide dependent chemical modifications of proteins. The level of nitrotyrosine can be elevated by the nitrative stress and is regarded as a marker for inflammation or some pathologies. Nitrotyrosine residues can be reduced to aminotyrosine in vivo and in vitro. Because protein molecules can catalyze auto-nitrosation by nitric oxide in aerobic conditions, it is proposed that these aminotyrosine residues could be diazotized in vivo yielding diazotyrosine-containing proteins. It is demonstrated herein that diazotyrosine residues in peptides and proteins have significant stability and can be identified as products of azo-coupling with naphthylamine derivatives. In MALDI-TOF mass-spectra these azodyes give a unique ion pattern of products due to (thermo)lysis of N=N bonds. Using biotinylated derivatives of naphthylamine and Western blotting diazotyrosine compounds in proteins can be identified at levels as low as about 1 ng.

Materials and Methods

Chemicals. All chemicals were of highest possible grade and used without additional purification unless otherwise specified. Bovine serum albumin, Fraction V, (BSA), sodium nitrite (NaNO$_2$), sodium dithionite (Na$_2$S$_2$O$_4$), sulfamic acid (NH$_2$SO$_3$H) were obtained from Sigma-Aldrich (St. Louis, Mo.), synthetic nitrotyrosine peptide was from Sigma.

N-(1-Naphthyl)ethylenediamine dihydrochloride (NEDA) (Sigma) and $N^1$-(1-Naphthyl),$N^2$-diethylethylenediamine oxalate (DENEDA) (Berlin-Chemi) were re-crystallized from hot ethanol-water mixture, tested for purity by TLC and stored in darkness.

L-Arginyl-NEDA (Arg-NEDA), Biotinyl-NEDA (Bio-NEDA) and Biotinyl-Arginyl-NEDA (Bio-Arg-NEDA) were synthesized by common procedures of peptide synthesis from NEDA-2HCl, Cbs-Arg, and Biotin. Briefly, Cbs-Arg was condensed with NEDA using DMF/$SOCl_2$ and amino group was deprotected using $HBr/CH_3COOH$ as described previously [33]. Biotinyl-derivatives were prepared from NEDA or Arg-NEDA and biotin using ethyl-3-[3-(dimethylamino)propyl]carbodiimide or succinimidyl D-biotinate (Sigma). All new compounds were purified by chromatography on Davisil silica-gel, grade 635 (Aldrich) and/or recrystallization and were characterized by common chemical methods.

TLC was performed using Silica-gel on aluminum plates (Sigma-Aldrich) and the spots were detected under UV by fluorescence of separated compounds.

Spectrophotometric measurements were made on Cecil CE 9500 UV-Vis spectrophotometer at room temperature.

Nitration and reduction of proteins and peptides. Proteins were nitrated by tetranitromethane according to previously published method with slight modifications [34, 35]. Briefly, 1 ml of 5 mg/ml bovine serum albumin (BSA) in 50 mM sodium phosphate buffer (pH 7.8) was stirred at 4° C. with 5 µl of tetranitromethane (heterogeneous mixture). After 2 h, the solution was centrifuged and the nitrated protein was separated from nitroformate using a size exclusion chromatography (Sephadex G-25). The yellow fraction of nitrated protein was collected and stored at 4° C. in the dark. The separation of nitroformate from peptides and low-molecular compounds was performed by chromatography on Silica-gel column.

The reduction of protein 3-nitrotyrosine to 3-aminotyrosine was accomplished by adding a freshly prepared solution of 0.25 M sodium dithionite ($Na_2S_2O_4$) to the solution of protein in sodium phosphate buffer at 25° C., followed by desalting the mixture on Sephadex G-25 column after few minutes of incubation [35, 36]. In the case of peptides and low-molecular nitrotyrosine compounds, removal of excess of the reductant was performed by addition of $SrCl_2$ solution and precipitation of the white pellet by centrifugation. Because aminotyrosine is light- and air-sensitive, reduced proteins or synthetic peptides usually were diazotized immediately after reduction. Otherwise, argon-purged solutions could be stored a few days at 0° C.

Diazotization and azo-coupling. In a typical procedure 200 µl of 2 M sodium nitrite was added to 10 ml of cold (<0° C.) 0.2 M HCl solution and mixed by stirring. Equal volumes of prechilled aminotyrosine-containing protein solution in 0.05 M sodium phosphate buffer and cold $HNO_2$/HCl solution were mixed on ice. The resulting yellowish solution was incubated on ice for 2 min, and 0.1 volume of 1 M sulfamic acid was added to remove the excess of nitrite. Usually, evolving nitrogen forms a foam or small bubbles. After 1 min the slightly yellowish solution of diazotyrosine containing protein does not contain nitrite and can be removed from ice.

A solution of NEDA or other target for azo-coupling in 0.05 M HCl or in DMF was added to the obtained solution of diazo-protein and mixture was incubated at 37°. After a few minutes a color change to blue or violet (the color is pH-sensitive—see Results) was observed. The development of azo-coupling reaction was monitored by absorption, usually at 540 nm. When the reaction was finished, the resulting azo-protein was separated from the excess of NEDA and byproducts using a Sephadex G-25 column. In near-neutral buffers the color changes to pink.

Tryptic hydrolysis of nitro- and azo-BSA was performed at 37° C. with a trypsin/protein ratio of ~1:20 (w/w) for 16 h according manufacturer protocol (Invitrogen). The tryptic hydrolyzates consisting of both unmodified and modified peptides were then filtered through a molecular membrane with a 3000 Da cut-off (Microcon YM-3, Millipore) and separated by reverse-phase HPLC.

HPLC separations were carried out using Waters 600 HPLC unit equipped and Water 2487 Dual λ Absorbance detector. Samples were separated on a reverse-phase Delta Pack $C_{18}$ column (Waters, cat #WAT036875) equipped with a guard column. All samples were analyzed by HPLC equipped with two optical detection channels. For detection of peptides we used wavelengths 215 nm and 280 nm, for nitrotyrosine contained products—340, 430 nm, for naphthylamine derivatives—280 nm and 340 nm, for azo-coupling products of diazotyrosine—500 nm and 580 nm. Peptides were loaded for 10 min at a flow rate of 0.5 mL/min in isocratic conditions of 5% of solvent B, then eluted with a 60 min 50%–80% gradient of solvent B. Both solvent A (0.1% TFA in water) and solvent B (0.08% TFA in acetonitrile) were purged continuously with helium. Fractions were collected and used for MS.

Mass Spectrometry Analyses. HPLC fractions were dried under vacuum and redissolved in 50% methanol with 1% formic acid. Aliquots of the solutions were deposited in gold/palladium-coated glass nanoelectrospray capillary tubes for analysis on a PerkinElmer Sciex API 3000 triple quadrupole mass spectrometer (Concord, Ontario, Canada) equipped with a Protana nanoelectrospray source (Odense, Denmark) and/or directly to the target plate of the ABI Voyager-DE STR MALDI—TOF mass spectrophotometer (Foster City, Calif.) using α-cyano-4-hydroxycinnamic acid (10 µg/µl) as matrix. The samples were analyzed by one or more of the following procedures. For determination of peptide molecular mass, full scan mass spectra were recorded utilizing either Q1 as the resolving analyzer in positive ion mode on the triple quadrupole instrument or by time of flight in the positive ion reflectron mode of analysis. Product ion spectra were acquired on the electrospray instrument utilizing Q1 to transmit the precursor ion of interest to the radio frequency-only collision cell Q2 under collisionally activated decomposition conditions. Nitrogen was the collision gas, and collision energies in the range of 20–50 eV product ions were analyzed using Q3 to determine the peptide sequence.

Development of modified samples in PAGE and PVDF. The samples were separated on 7.5% PAGE and the colorimetric development was performed directly in gel or after the transfer of proteins on PVDF membrane. The reduction, diazotization and azo-coupling were carried out similar to protocols in solution. Extensive washes were performed between steps. Because of a slow diffusion rate of reagents into the gels, reaction times and washings were increased.

Western blotting. Proteins azo-coupled with Bio-NEDA and Bio-Arg-NEDA were transferred from 7.5% PAG (polyacrylamide gel) on PVDF membrane and the presence of coupling was determined by Western blotting using anti-biotin HRP-conjugated antibodies at dilution of 1:800 in 5% non-fat dried milk. The signal was developed with ECL plus reagent according to the manufacture's instructions.

Results and Discussion

Rationale. Nitrosation and nitration are the main NO-dependent protein modifications. We formed the hypothesis that if the nitration of tyrosine residues and their subsequent reduction to aminotyrosine are ordinary biochemical processes, then a diazotization of the aminotyrosine by natural nitrosants (products of nitric oxide oxidation or nitrite in acid solutions) might yield diazotyrosine residues in proteins. Surprisingly, although diazotyrosine derivatives are easily generated by chemical synthesis [37] and o-diazophenol compounds have found broad industrial applications (mostly as dyes and precursors of quinone diazides, used in microelectronics) [38-40], there appears to be no information about diazotyrosine in proteins. High reactivity (including reactions with side-groups of the same proteins) and very low steady state concentrations of such derivatives, and their apparent instability, as well as an apparent lack of any purposeful searching for these protein modifications, may also have contributed to the deficiency of information.

Diazotization of aminotyrosine residues in proteins. We obtained diazotyrosine derivatives of proteins according to the Scheme 1, shown in FIG. 1A, and as described in *Material and Methods*. It was found that the diazotyrosine derivatives are more stable than their low-molecular weight analogs. First, we investigated the approaches for quantification of these derivatives. It should be noted that since both nitro- and aminotyrosine residues (I, II, respectively, in Scheme 1 (FIG. 1A)) can be converted to diazotyrosine derivatives (III), these approaches may be common for nitrotyrosine- and aminotyrosine-containing proteins.

A reaction of azo-coupling of diazotized arylamines with derivates of naphthylamine (Griess reaction) has broad application for the colorimetric quantification of both aryl amines and nitrite. We carried out a representative test for the quantification of diazotyrosine derivatives, as follows.

Figure 2C:
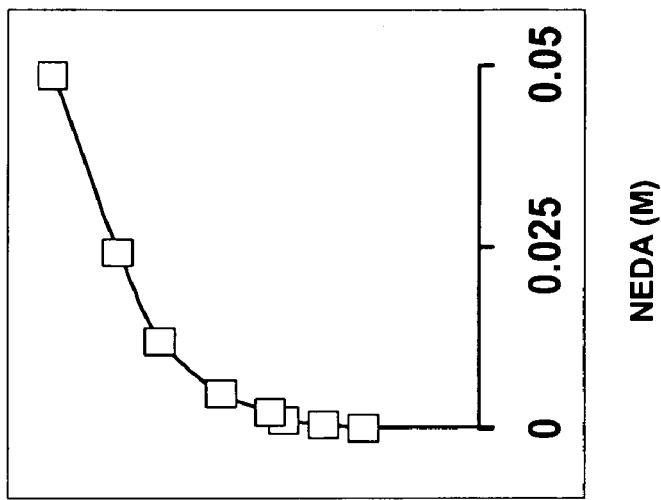
FIGS. 2A–C are graphs showing the dependence of the yield of BSA-NEDA azodye on the reaction conditions.
Figure 2B:
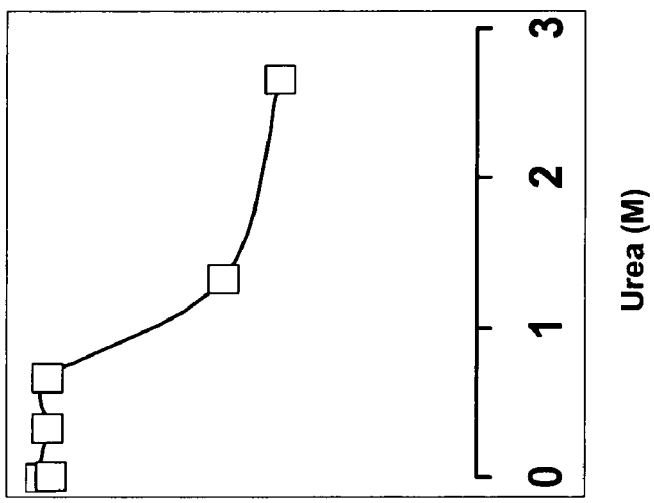
Figure 2A:
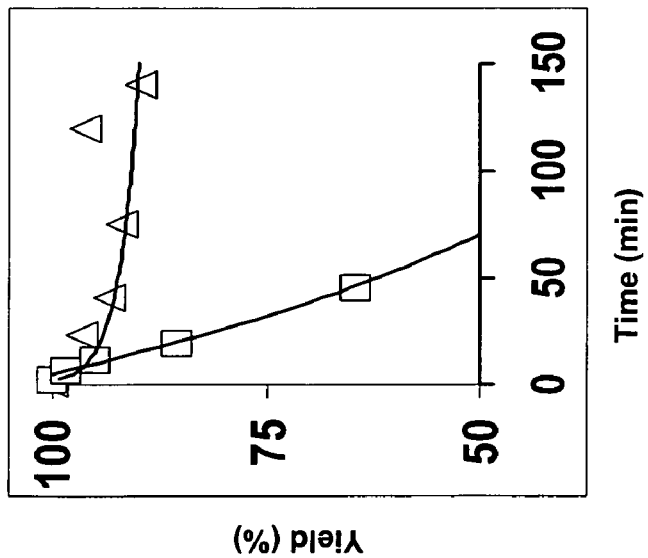

In this reaction we predicted that diazotization of an aminocompound would yield a diazonium cation capable of reacting with substituted naphthylamine to generate a dye. Indeed, in our tests a colorless solution of aminotyrosine-containing BSA ($H_2N$-Tyr-BSA, Scheme 1, II) diazotized in HCl solutions, and formed a yellowish solution of, presumably, BSA containing diazotyrosine ($^+N=N$-BSA, Scheme 1, III). As predicted, the following reaction with 1-(naphthyl) ethylendiamine (NEDA, IV, R=$NH_2$) yielded a BSA solution containing a blue dye, presumably the azodyes V (azo-BSA) in Scheme 1 (FIG. 1A). The color of the reaction product is pH-sensitive. At low pH (<2) the product appears blue (max at 580 nm), but at higher pH the products appears pink (max at 500 nm). These spectral properties allow us to directly monitor the formation of the reaction product and could be used to selectively isolate peptides or proteins with diazotrosine modification. More specifically, FIGS. 2A–C are graphs showing the dependence of the yield of BSA-NEDA azodye on the reaction conditions. $NH_2$-BSA solution was nitrosated by $NaNO_2$/HCl at 0° C. and the excess of nitrite was removed by addition of sulfamate. NEDA was added and the mixtures were incubated at 37° for 2–12 hours. The formation of BSA-NEDA azodyes is monitored by measuring the absorption at 500 nm of 5 fold-diluted aliquots. Results are normalized to the highest yield in the series. Referring to FIG. 2A, the squares indicate the effects of nitrosation time on the yield of BSA-NEDA at 0°. $NH_2$-BSA was incubated with $NaNO_2$HCl. At different time points aliquots were taken and nitrosation reaction was stopped by addition of sulfamate. After the completion of the time course, aliquots were supplied with NEDA, incubated for 2 hours at 37° C. and the formation of BSA-NEDA detected. In FIG. 2A, the triangles indicate stability of diazo-BSA after the removal of nitrites was monitored by varying the incubation times with sulfamate at 37° C. before addition of BSA-NEDA. In FIG. 2B the effect of urea on the efficiency of nitrosation is shown. $NH_2$-BSA was supplied with various concentrations of urea before addition of $NaNO_2$HCl. Sulfamate solution was added 2 mm later and azo-coupling with NEDA performed as described. FIG. 2C shows the effect of NEDA concentration on the efficiency of azo-coupling. The yield of BSA-NEDA was measured 12 hours after addition of NEDA.

Monitoring spectroscopically the formation of blue dyes in the model BSA protein after reaction with NEDA, we optimized the conditions for diazotization (reaction (II) in Scheme 1) and investigated the stability of diazotyrosine product in proteins. Low temperatures, short reaction times and low pH were found to be optimal for diazotization of BSA containing aminotyrosine. E.g., at 0° C. in 0.04 M $NaNO_2$/0.2 M HCl/0.025 M phosphate solution diazotization of $H_2N$-Tyr-BSA and formation of $^+N=N$-BSA was complete in under a minute. These reaction times are rather short, when compared with usual conditions for production of azodyes [38, 40]. It should be noted that at neutral and basic pH, a photo-reactive quinone diazide (Scheme 1, IIIa) could be formed and it could interfere with the yield of final azodye.

Prolonged incubation of $+N=N$-BSA with even 0.04 M nitrite at 0° C. significantly decreased the yield of subsequent azo-coupling reaction with NEDA and formation of azo-BSA FIG. 2C). To remove the excess of nitrite after diazotization, we used sulfamic acid, which reacts with nitrite yielding nitrogen. Interestingly, urea, which is used to remove nitrites in industrial procedure of azo dyes synthesis [40], was not effective in this case. For additional details, see the description of FIG. 2B in the Description of the Drawings, above.

Under the reaction conditions not only aminotyrosine, but also amidogroups, e.g. sulfamic acid, could react with nitrite. Primary amides can be nitrosated irreversibly yielding nitrogen and carboxyl as follows: $CO-NH_2+NO^{30} = COOH+N_2+H^+$. However, diazotization of $H_2N$-Tyr-BSA can be done in a large excess of urea, commonly used for protein denaturation (FIG. 2C).

To check whether protein amide groups could react with diazotization of aminotyrosine we used the following synthetic peptide Ac-LAAAGY($NO_2$)DVEKNNSRCON$H_2$, M=1593. This peptide has a broad combination of side-groups susceptible to nitrosation, including three CO—$NH_2$ groups of Asn and Arg-amide, $H_2N$-group of lysine, guanidine of Arg, HO— of Ser, two HOOC— of Asp and Glu and CO—NH groups of peptide bonds. The carboxy-group of Asp and Glu nitrosates extremely fast, but resulting nitroso-carboxylates are unstable. However, they may be used to catalyze nitrosation of other groups [41]. At low pH amino- and guanidino-groups are protonated and should have low reactivity. Peptide CO—NH groups and HO-group of Ser could be nitrosated, but the reactions are reversible. In this case, even if the RONO groups are formed, in acidic conditions addition of sulfamate will shift the RONO$\leftrightarrow NO_2^-$ equilibrium, and quickly decrease the RONO concentration. To test the effects of nitrozation on protein amidogroups, we reduced the peptide's nitrotyrosine to aminotyrosine, and then diazotized it as described in herein. The azo-coupling with several substituted naphthylamines (Scheme 1, IV) resulted in blue azo-peptides, which were separated from the excess of reagents by HPLC and analyzed by mass-spectra.

Figure 3:
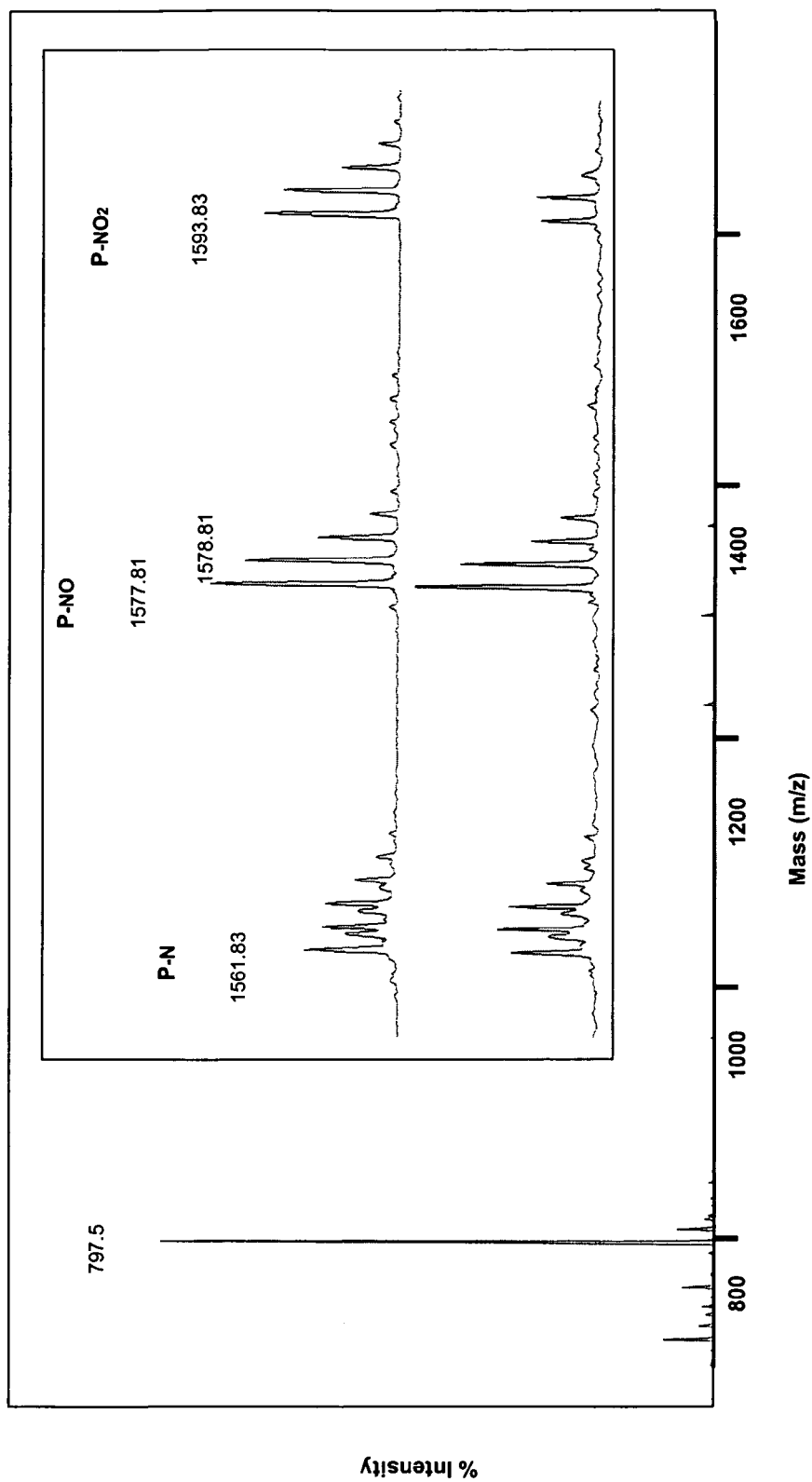
FIG. 3 is a graph showing the ion-spray mass spectrum of the nitro-peptide Ac-LAAAGY(NO$_2$)DVEKNNSR—CONH$_2$ (M=1593) and the MALDI mass spectrum of the same peptide (inset, upper spectra).

Mass-spectral analysis of diazotyrosine-containing peptide. When nanospray MS analysis was used, we found the expected molecular ion at 797.5 corresponding to the $(M+2H^+)$ mode of unmodified peptide, and few small signals, corresponding to higher ionization modes of the peptide (FIG. 3). In MALDI-TOF MS analysis of unmodified nitrotyrosine-containing peptides the molecular ions $(M+H)^+$ are accompanying a group of ions $[M+H-14 (-O+2H)]^+$, $[M+H-16 (-O)]^+$, $[M+H-30 (-2O+2H)]^+$ and $[M+H-32 (-2O)]^+$, which are reduction products [44, 45].

We found an analogous combination of ions for our studied nitropeptide (FIG. 3, inset). Under reflectron conditions an abundant protonated molecular ion at m/z 1593.80, as well as several lower mass ions at m/z 1577.81 [−O], 1561.83 [−2O] and 1563.83 [−2O, +2H] were detected. In addition to this pseudo-triplet, a few small and unfocused ions are seen in the reflectron spectrum, suggesting that various metastable processes are also occurring. In addition, we observed an ion at 1562.51 [(M+H)−31.29], which is located between the m/z 1561.83 ion and its $^{13}$C (or $^{15}$N, or $^{2}$H, or $^{17}$O) isotopomer at m/z 1562.82, and whose mass is inconsistent with the elemental composition of the peptide. The similar ion with m/z [(M+H)−31.7] was also observed for other nitrotyrosine containing peptide [42]. More specifically, FIG. 3 shows the ion-spray mass spectrum of the nitro-peptide Ac-LAAAGY(NO$_2$)DVEKNNSR—CONH$_2$ (M=1593) and the MALDI mass spectrum of the same peptide (inset, upper spectra). In MALDI the molecular ions are shown as P—NO$_2$ (1593.83 and isotopomers), and reduction products are shown as P—NO (1577.81 and isotopomers) and P—N (1561.83 and isotopomers). The complex combination of ions of P—N region should be noted in particular. The MALDI spectrum of partly reduced sample of the nitro-peptide (probably a mixture of nitro- and nitroso-forms) after HPLC-separation is shown in a lower panel of the inset). P—NO$_2$ ions are reduced, but P—NO and P—N did not change.

Figure 4A:
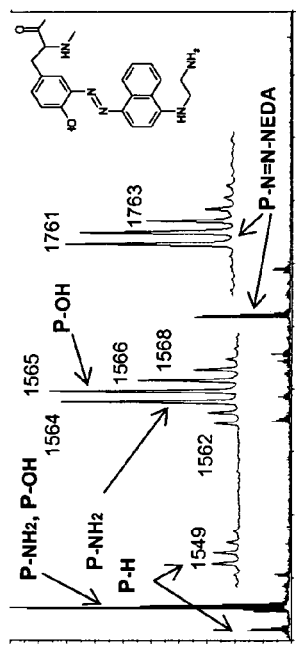
FIGS. 4A–C are graphs showing the MALDI mass spectra of azo-peptide dyes with NEDA (FIG. 4A), DENEDA (FIG. 4B) and Arg-NEDA (FIG. 4C). Ions of unmodified tyrosine, H$_2$N-Tyr, HO-Tyr (3,4-dihydroxy-phenylalanine) residues are marked as P—H, P—NH$_2$, P—OH, respectively. The insets shows P—H, —P—OH regions (left) and molecular ions regions (right) at higher scales, which are different both in abscissa and ordinate.
Figure 4B:
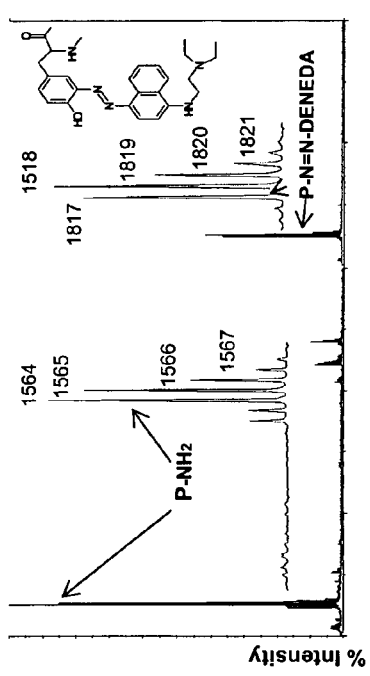
Figure 4C:
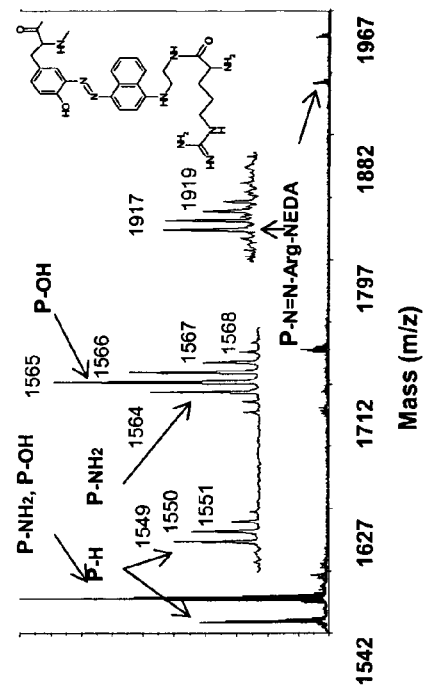

Referring now to FIGS. 4A–C, MALDI-TOF mass-spectra of azo-coupling products of diazo-peptide with three substituted naphthylamines IV (R=NH$_2$ (FIG. 4A), NEt$_2$ (FIG. 4B), NH-Arg (FIG. 4C),) are shown. Ions of unmodified tyrosine, H$_2$N-Tyr, HO-Tyr (3,4-dihydroxy-phenylalanine) residues are marked as P—H, P—NH$_2$, P—OH, respectively. The insets shows P—H, —P—OH regions (left) and molecular ions regions (right) at higher scales, which are different both in abscissa and ordinate. Due to overlapping P—NH$_2$ and P—OH regions, 1564.85–1564.88 (shown as 1565) ions are the summa of P—OH molecular ion and P—NH$_2$ isotopomers with one additional neutron ($^{13}$C, $^{15}$N or $^{17}$O). If an impact of P—OH is small, so the signal of 1563.86–1563.89 (shown as 1564) ion (P—NH$_2$ only) is larger, then signals of 1565 ions (P—NH$_2$ isotopomers and P—OH) (see left inset in B), if an impact of P—OH is significant, so the first peak (1564 ion —P—NH$_2$ only) is smaller, then the second (signals of 1564.85–1564.88 ions (P—NH$_2$ isotopomers and P—OH)) (see left insets in A and C). It should be noted that the correlation between P—H and P—OH signals (P—H and P—OH are proportional to each other. Two small peaks to the left from P—NH$_2$ ion (the first shown as 1562 in A) could be nitren or quinone-imin (first) and their isotopomers or o-quinone (second). More specifically, molecular ions 1761 (Va), 1817 (Vb), and 1917 (Vc) of these three azodyes (shown in FIGS. 4A, 4B and 4C, respectively) are accompanying the main group of ions at (M−30) and (M−29) (marked as P—NH$_2$ and P—OH; M is a mass of nitrated peptide), which is similar for all three compounds, and (M−45) ion of the non-nitrated peptide (marked as P—H). The signals of P—H and P—NH$_2$ ions are small at R=NEt$_2$ and large for two other dyes. With nanospray MS we found molecular ions at 441 (Va), 606.5, 455 (Vb) and 640, 480 (Vc) as well as few additional ions (data not shown). The main signals of azodyes ions in nanospray spectra were in (+3H$^+$) and (+4H$^+$) modes because all used naphthylamine compounds IV had addition positive-charged groups. Strong signals of molecular ions of azodyes Va, Vb, Vc with a predicted distribution of isotopomers and a lack of +1-shifts (NH$_2$→OH) for these ions indicated that (1) we are able to change a nitro-group of nitrotyrosine residue on diazonaphthylamine groups with addition substitute reporter groups (R), and (2) that in our diazotization/azo-coupling conditions there were no significant modifications of other amino-, amido-, guanidino- and other side-groups of the peptide.

Figure 1B:
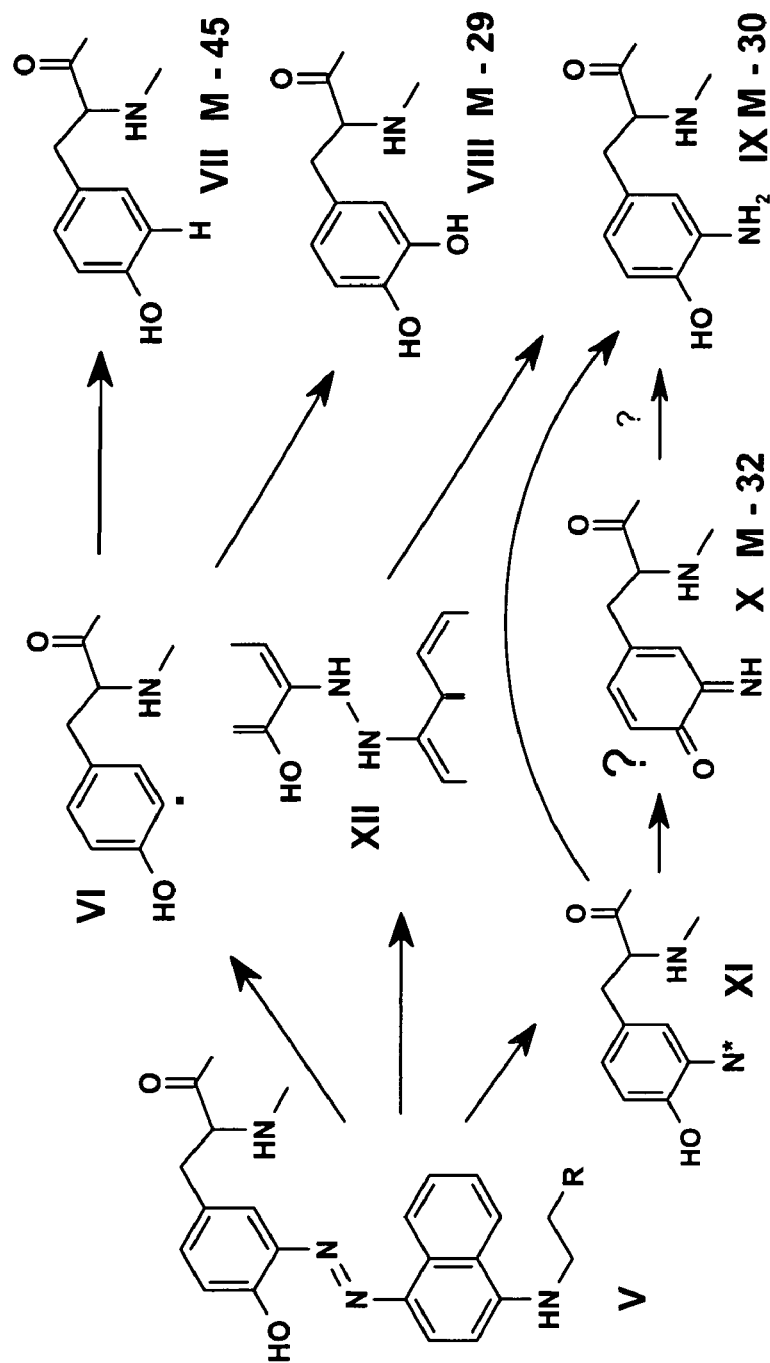

The presence of P—H, P—NH$_2$, and P—OH ions in all MALDI spectra of azodyes indicated that N=N bond of V has low stability under the conditions of the laser-assisted evaporation-ionization of the samples. Referring now to Scheme 2, shown in FIG. 1B, free-radical product of photolysis VI is either partially reduced to peptide with non-nitrated tyrosine VII (P—H), or partially oxidized to catechol derivative VIII (P—OH).

A competing path exists for aminotyrosine derivative IX (P—NH$_2$), probably through hydrazino-compound XII. Indeed, if nitren XI would be intermediate, so its uncharacterized stable isomers X (M−32, shown as quinone-imine derivatives), which we observed in MALDI MS of nitrotyrosine containing peptide I, must be one of the main products. However in all three spectra of Va, Vb, Vc both (M−32) and (M−31) ions (1562 and 1563) are much smaller than (M−30) ion. (Alternatively, nitren XI is not intermediate by photo-reduction of I, and for detectable ions X (M−32) in the spectra of nitrotyrosine peptides exists an alternative pathway.)

These results demonstrate that nitrotyrosine containing peptides, their reduced forms, as well as their diazotyrosine derivatives can be identified by MALDI MS of azo-tyrosine dyes using the aminotyrosine/catechol doublets (P—NH$_2$ and P—OH) accompanying signals of peptide with non-modified tyrosine (P—H) and a molecular ion of azodye.

It has been previously shown that the pattern of reduced products for nitrotyrosine containing peptides is matrix-sensitive. When a 2,4,6-trihydroxyacetophenone-nitrocellulose matrix (THAP- NC) was used, the yield of (M+H−30)$^+$ and (M+H−32)$^+$ ions was very small compared to cyano-4-hydroxycinnamic acid [43]. It is possible that the matrix plays a role of reductant during the laser assisted evaporation-ionization. In this case it is likely that a change of matrix can affect the competing path of diazotyrosine azodyes fragmentation in MALDI as well.

Of all the amino acids, only tyrosine, tryptophan, and histidine can react with reactive aryldiazonium salts at neutral pH. Thus, these residues could react with newly produced protein azotyrosine and affect NEDA derivatization of azotyrosine. In this case only azotyrosine residues that do not have in their vicinity His, Trp or Tyr residues could be available for azo-coupling with NEDA. However, if the induction of azotyrosine is produced after the protein denaturation the impact of such intramolecular azo coupling could be lower. Moreover, this intramolecular azo coupling could be further decreased if the formation of protein azotyrosine is performed at acidic pH, when Tyr, Trp or His residues are protonated and less reactive.

We tested this hypothesis by preincubating diazo-BSA for one hour with an excess of Tyr, Trp or His amino acids and their derivatives in acidic solutions. No azo-coupling was detected, as determined by absence of changes in UV-Vis spectra Moreover, the yield of the following azo-coupling reaction with NEDA or DENEDA, monitored by absorbance at 580 nm, was not affected by these preincubations. In a different approach, preincubation of diazo-BSA with 15–80 kDa polymers poly-His, poly-Tre, poly-(Lys, Phe), poly (Arg, Pro, Tre) did not affect the mobility of diazo-BSA on the PAGE, suggesting the lack of azo-coupling. These results indicate that in tested conditions diazotyrosine residues have low reactivity and do not react with other amino acids, although they effectively react with NEDA.

Figures 5A, 5B:
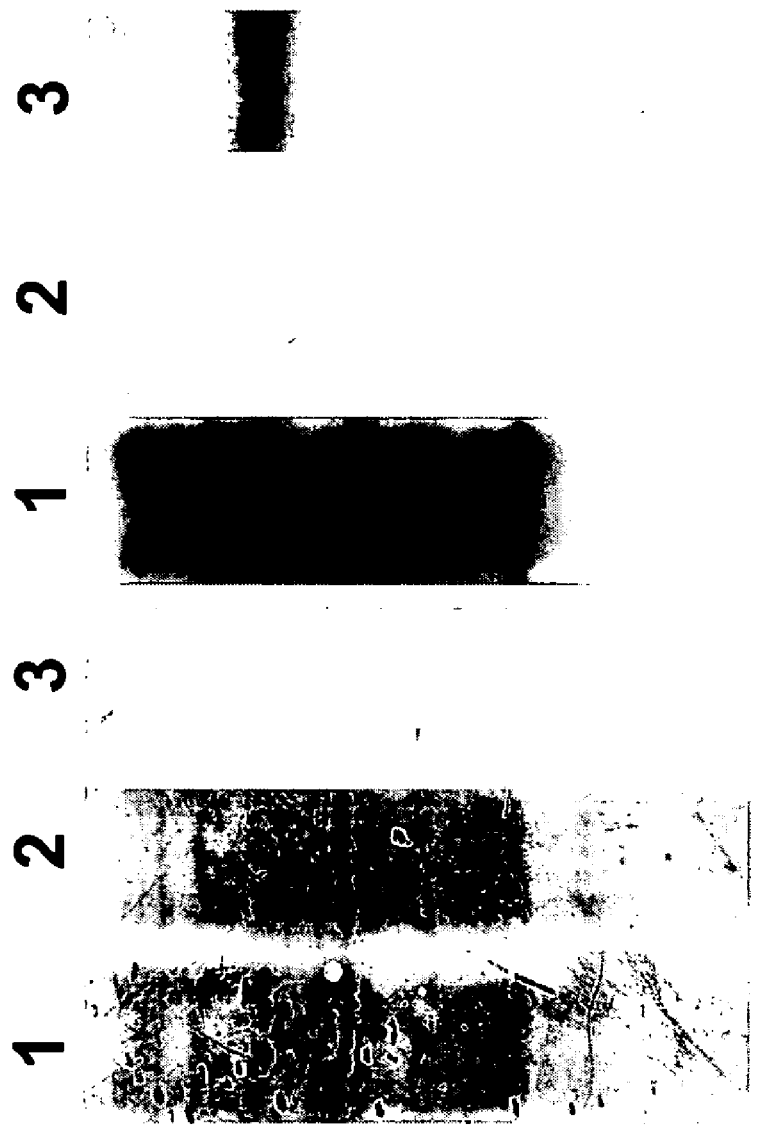
FIGS. 5A–B are photographs of polyacrylamide gel electrophoresis patterns showing the detection of diazotyrosine by Western blot (WB). Lysate of RAW cells (columns 1, 2) and nitro-BSA (column 3) were separated by PAGE and proteins were transferred on PVDF membrane. Membrane was preincubated with Bio-NEDA and then developed by HRP-WB (column 1); Membrane was developed by HRP-WB without Bio-NEDA (column 2). Membrane was reduced by Na$_2$S$_2$O$_4$, diazotized, preincubated with Bio-NEDA, and developed by HRP—WB (column 3).

Improving the sensitivity of diazotyrozine detection. To increase the sensitivity of detection of coupled products we used biotin as the substitute R (Scheme 1, IV and V). Using anti-biotin HRP-conjugated antibodies we were able to identify ~1 ng of nitro-BSA after reaction with Bio-NEDA (FIG. 5A) and Bio-Arg-NEDA (not shown). To determine if diazotyrosine-containing proteins occur in vivo, we transferred on PVDF membrane proteins from lysate of RAW cells separated by PAGE. When these membranes were incubated with Bio-NEDA for azo-coupling, and developed by WB multiple protein species were detected (FIG. 5B). When Bio-NEDA was omitted no signals were observed, indicating the specificity of the analysis. Similar data were obtained with Bio-Arg-NEDA (data not shown). Clearly, the same approach can be used for identification of small concentrations of nitro-tyrosine containing proteins. In this case the membrane has to be reduced and diazotized before azo-coupling. As an example, in line 3 WB-detection of nitro-BSA is shown. In FIGS. 5A–B, lanes 1 and 2 are the lysate of RAW cells. Lane 3 is the Nitro-BSA compound. Treatments were as follows: Membrane was preincubated with Bio-NEDA, then developed by HRP-WB (lane 1); membrane was developed by HRP-WB (lane 2); or membrane was reduced by $Na_2S_2O_4$, diazotized, preincubated with Bio-NEDA, then developed by HRP—WB (lane 3). In FIG. 5A the membrane was stained with Coomassie, and in FIG. 5B the Western blots are shown.

NEDA-mediated biotinylation of diazotyrosine can be also used to separate and concentrate diazotyrosine containing proteins or peptides (as well as their nitro-, nitroso-, hydroxyamino- and amino-precursors) on streptavidine columns. The feasibility of such approach was demonstrated [36], when aminotyrosine-containing human serum albumin (HSA), derived from nitrated HSA was acylated at pH 5 by sulfo-NHS-SS-Biotin.

Apart from tyrosine, there are other natural targets for in vivo nitration both in proteins (trypthophan [4, 44], histidine [45]) and nucleic acids (guanosine [47, 48]). All of those natural targets may be reduced (even in vivo [27]), then diazotized and identified by the same or similar methods as described herein. The present examples are considered representative of methods and compositions employing other natural targets, and the scope of the present invention is intended to encompass all such natural targets for in vivo nitration.

In the present disclosure it is shown that diazotyrosine residues in the proteins are rather stable and their azo-coupling products (azo-tyrosine derivatives) can be used for identification and quantification of nitro- and aminotyrosine containing proteins. Nitrosation of these latter in vivo could be a natural source of diazotyrosine for all nitric oxide producing organisms. Its reactivity should be taken into consideration to understand the metabolism of nitrogen oxides, for treatment of pathologies and illness, for which the high level of nitrotyrosine in proteins is known, such as inflammation, asthma, Parkinsonism, Alzheimer's disease, ischemia, cancer, and other diseases.

Without further elaboration, it is believed that one skilled in the art can, using the description herein, utilize the present invention to its fullest extent. The foregoing embodiments are to be construed as illustrative, and not as constraining the remainder of the disclosure in any way whatsoever. While the preferred embodiments of the invention have been shown and described, modifications thereof can be made by one skilled in the art without departing from the spirit and teachings of the invention. The embodiments described herein are exemplary only, and are not intended to be limiting. Many variations and modifications of the invention disclosed herein are possible and are within the scope of the invention. For example, just as the chemistry of o-hydroxy-diazocompounds and their quinone diazide isomers have shown broad applications for the photo and microelectronic industries, the disclosed chemistry, methods, compositions and technical design are expected to find use in a variety of applications in biochemistry, proteomics, and molecular medicine.

Without further elaboration, it is believed that one skilled in the art can, using the description herein, utilize the present invention to its fullest extent. The foregoing embodiments are to be construed as illustrative, and not as constraining the remainder of the disclosure in any way whatsoever. While the preferred embodiments of the invention have been shown and described, modifications thereof can be made by one skilled in the art without departing from the spirit and teachings of the invention. Many variations and modifications of the invention disclosed herein are possible and are within the scope of the invention. Accordingly, the scope of protection is not limited by the description set out above, but is only limited by the claims which follow, that scope including all equivalents of the subject matter of the claims. The disclosures of all patents, patent applications and publications cited herein are hereby incorporated herein by reference, to the extent that they provide exemplary, procedural or other details supplementary to those set forth herein.

REFERENCES

1. Beckman, J. S., Ischiropoulos, H., Zhu, L., van der Woerd, M., Smith, C. D., Harrison, J., Martin, J. C. & Tsai, J-H. M. (1992) *Arch. Biochem. Biophys.* 298, 438–445.
2. Reiter, C. D., Teng, R. J. & Beckman, J. S. (2000) *J. Biol. Chem.* 275, 32460–32466.
3. Sawa, T., Akaike, T. & Maeda, H. (2000) *J. Biol. Chem.* 275, 32467–32474.
4. Kikugawa, K., Kato, T. & Okamoto, Y. (1994) *Free Radical Biol. Med.* 16, 373–382.
5. Van der Vliet, A., Eiserich, J. P., Halliwell, B., & Cross, C. E. (1995) *Arch. Biochem. Biophys.* 319, 341–349.
6. Goldstein, S., Czapski, G., Lind, J. & Merenyi, G. (2000) *J. Biol. Chem.* 275, 3031–3036.
7. Zhang, H., Joseph, J., Felix, C. & Kalyanaraman, B. (2000) *J. Biol. Chem.* 275, 14038–14045.
8. Zhang, H., Bhargava, K., Keszler, A., Feix, J., Hogg, N., Joseph, J. & Kalyanaraman, B. (2003) *J. Biol. Chem.* 278, 8969–8978.
9. Van der Vliet, A., Eiserich, J. P., Halliwell, B. & Cross, C. E. (1997) *J. Biol. Chem.* 272, 7617–7625.
10. Baldus, S., Eiserich, J. P., Mani, A., Castro, L., Figueroa, M., Chumley, P., Ma, W., Tousson, A., White, C. R., Bullard, D. C., et al., (2001) *J. Clin. Invest.* 108, 1759–1770.
11. Wu, W., Chen, Y. & Hazen, S. L. (1999) *J. Biol. Chem.* 274, 25933–25944.
12. Gaut, J. P., Byun, J., Tran, H. D., Lauber, W. M., Carroll, J. A., Hotchkiss, R. S., Belaaouaj, A. & Heinecke, J. W. (2002) *J. Clin. Invest.* 109, 1311–1319.
13. Thomas, D. D., Espey, M. G., Vitek, M. P., Miranda, K. M. & Wink, D. A. (2002) *Proc. Natl. Acad. Sci. USA.* 99, 12691–12696.
14. Bian, K., Gao, Z., Weisbrodt, N. & Murad, F. (2003) *Proc. Natl. Acad. Sci. USA.* 100, 5712–5717.
15. Miyagi, M., Sakaguchi, H., Darrow, R. M., Yan, L., West, K. A., Aulak, K. S., Stuehr, D. J., Hollyfield, J. G., Organisciak, D. T. & Crabb, J. W. (2002) *Mol. Cell. Proteomics.* 1, 293–303.
16. Andreadis, A. A., Hazen, S. L., Comhair, S. A. & Erzurum, S. C. (2003) *Free Radic. Biol. Med.* 35, 213–225.
17. Shishehbor, M. H., Aviles, R. J., Brennan, M. L., Fu, X., Goormastic, M., Pearce, G. L., Gokce, N., Keaney, J. F., Jr., Penn, M, S., Sprecher, D. L., Vita, J. A. & Hazen, S. L. (2003) *JAMA* 289, 1675–1680.
18. Castegna, A., Thongboonkerd, V., Klein, J. B., Lynn, B., Markesbery, W. R. & Butterfield, D. A. (2003) *J. Neurochem.* 85, 1394–1401.
19. Giasson, B. I., Duda, J. E., Murray, I. V., Chen, Q., Souza, J. M., Hurtig, H. I., Ischiropoulos, H., Trojanowski, J. Q. & Lee, V. M. (2000) *Science* 290, 985–989.
20. Dawson, T. M. & Dawson, V. L. (2003) *Science* 302, 819–822.
21. Ehsan, A., Sommer, F., Schmidt, A., Klotz, T., Koslowski, J., Niggemann, S., Jacobs, G., Engelmann, U., Addicks, K. & Bloch, W. (2002) *Cancer* 95, 2293–2301.
22. Herrero, M. B., de Lamirande, E. & Gagnon, C. (2001) *Mol. Hum. Reprod.* 7, 913–921.
23. Kuo, W. N., Kanadia, R. N., Shanbhag, V. P. & Toro, R. (1999) *Mol. Cell. Biochem.* 201, 11–16.
24. Kuo, W. N. & Kocis, J. M. (2002) *Mol. Cell. Biochem.* 233, 57–63.
25. Irie, Y., Saeki, M., Kamisaki, Y., Martin, E. & Murad, F. (2003) *Proc. Natl. Acad. Sci. USA* 100, 5634–5639.
26. Kamisaki, Y., Wada, K., Bian, K., Balabanli, B., Davis, K., Martin, E., Behbod, F., Lee Y.-C. & Murad, F. (1998) *Proc. Natl. Acad. Sci. USA* 95, 11584–11589.
27. Chen, H. J., Chen, Y. M. & Chang, C. M. (2002) *Chem. Biol. Interact.* 140, 199–213.
28. Sodum, R. S. & Fiala, E. S. (1997) *Chem. Res. Toxicol.* 10, 1420–1426.
29. Turko, I. V. & Murad, F. (2002) *Pharmacol. Rev.* 54, 619–634.
30. Gordin, V. A. & Nedospasov, A. A. (1998) *FEBS Lett.* 424, 239–242.
31. Beda, N. V., Suntsova, T. P. (1999) *FEBS Lett.* 453, 229–235.
32. Nedospasov, A. A. (2002) *J. Biochem. Mol. Toxicol.* 16, 109–120.
33. Kazantsev, A. G., Kuznetsov, N. V., Yakhimovich, A. D., Sharina, I. G., Nezavibat'ko, V. N. & Nedospasov, A. A. (1994) *Biochemistry (Moscow)* 59, 1139–1144.
34. Sokolovsky, M., Riordan, J. F., & Vallee, B. L. (1967) *Biochem. Biophys. Res. Commun.* 27, 20–25.
35. Sokolovsky, M. Riordan J. F. & Vallee, B. L. (1966) *Biochemistry* 5, 3582–3589.
36. Nikov, G., Bhat, V., Wishnok, J. S. & Tannenbaum, S. R. (2003) *Anal. Biochem.*, 320, 214–222.
37. Colas, C. & Goeldner, M. *Eur. J. Org. Chem.* 1999, 1357–1366.
38. Zollinger, H. Diazo chemistry. Vol. 1. VCH, New York, 1994.
39. Ershov, V. V., Nikiforov, G. A., De Jonge, C. R. H. I. Quinone diazides. Elsevier, Amsterdam. 1981.
40. Zollinger, H. Color chemistry. Syntheses, properties and applications of organic dyes and pigments. $2^{nd}$. Ed. VCH, Weinheim. 1991.
41. Casado, J., Castro, A., Mosquera, M., Prieto, M. F. R. & Tato, J. V. (1984) *Monatsh. Chem.* 115, 669–682.
42. Sarver, A., Scheffler, N. K., Shetlar, M. D. & Gibson, B. W. (2001) *J. Am. Soc. Mass Spectrom.* 12, 439–448.
43. Petersson, A. S., Steen, H., Kalume, D. E., Caidahl, K. & Roepstorff, P. (2001) *J. Mass. Spectrom.* 36, 616–625.
44. Alvarez, B., Rubbo, H., Kirk, M., Barnes, S., Freeman, B. A. & Radi, R. (1996) *Chem. Res. Toxicol.* 9, 390–396.
45. Sato, M., Nakano, T., Takeuchi, M., Kumagai, T., Kanno, N., Nagahisa, E. & Sato, Y. (1995) *Biosci. Biotechnol. Biochem.* 59, 1208–1210.
46. Shafirovich, V., Mock, S., Kolbanovskiy, A. & Geacintov, N. E. (2002) *Chem. Res. Toxicol.* 15, 591–597.
48. Akaike, T., Okamoto, S., Sawa, T., Yoshitake, J., Tamura, F., Ichimori, K., Miyazaki, K., Sasamoto, K. & Maeda, H. (2003) *Proc. Natl. Acad. Sci. USA*. 100, 685–690.

What is claimed is:

1. A method of quantifying and/or identifying a nitroderivative compound, or residue thereof, comprising:
   providing a sample comprising a protein, peptide or nucleic acid containing said nitroderivative compound, or residue thereof, in the form of a diazo compound or residue thereof;
   azo-coupling said diazo compound, or residue thereof to a target compound capable of producing a detectable signal, to yield an azo-coupled complex;
   quantitating and/or detecting said signal, to yield a quantitation and/or detection result; and
   determining from said quantitation and/or detection result the identity and/or concentration of said nitroderivative compound, or residue thereof in said sample.

2. The method of claim 1 comprising isolating said protein, peptide or nucleic acid containing said nitroderivative compound, or residue thereof, prior to said azo-coupling, or isolating said azo-coupled complex after said azo-coupling.

3. The method of claim 1 wherein said sample comprises a protein or peptide.

4. The method of claim 3, wherein said nitroderivative compound, or residue thereof is chosen from the group consisting of nitrotyrosine, aminotyrosine, and diazotyrosine, and residues thereof.

5. The method of claim 1, wherein said nitioderivative compound, or residue thereof is derived from an amino acid or nucleic acid chosen from the group consisting of tyrosine, tryptophan, histidine, and guanosine.

6. The method of claim 1 wherein said providing comprises converting said nitroderivative compound, or residue thereof, to a diazo compound, or residue thereof.

7. The method of claim 6 wherein said providing comprises reducing said nitroderivative compound, or residue thereof, prior to said converting.

8. The method of claim 6 wherein said nitroderivative compound is nitrotyrosine and said method comprises reducing said nitrotyrosine, or residue thereof, to an aminotyrosine compound, or residue thereof.

9. The method of claim 1 wherein quantitating and/or detecting said signal comprises spectral or colorimetric monitoring of an azo-coupling reaction.

10. The method of claim 9 wherein said spectral monitoring comprises mass-spectral or fluorometric monitoring of said azo-coupling reaction.

11. The method of claim 1 wherein the target compound of said azo-coupling step comprises a synthetic molecule.

12. The method of claim 11 wherein the synthetic target molecule contains a naphthyl moiety.

13. A method of detecting illness or disease in a mammalian subject comprising:
   carrying out the method of claim 1, wherein said sample is a biological sample from said subject; and
   determining fain said identification and/or concentration of said nitroderivative compound, or residue thereof in said sample, the presence and/or level of illness or disease in said subject.

14. A method to aid in diagnosing in a mammalian subject a pathology associated with a nitroderivative compound, the method comprising:

carrying out the method of claim 1; and determining from said identity and/or concentration of nitroderivative compound, or residue thereof in said subject a diagnosis as to said pathology.

15. The method of claim 14 wherein said pathology is chosen from the group consisting of asthma, atherosclerosis, inflammation, ischemia, Alzheimer's disease, Parkinson's disease and cancer.

16. The method of claim 1 wherein said nitroderivative compound, or residue thereof, is chosen from the group consisting of nitrosotyrosine and hydroxyaminotyrosine.

17. The method of claim 1 wherein said target compound comprises biotinyl-NEDA or biotinyl-arginyl-NEDA, wherein NEDA is N-(1-Naphthyl)ethylenediamine dihydrochloride.

18. A method of quantifying and/or identifying a nitroderivative compound, or residue thereof, comprising:

providing a biological sample containing at least one nitroderivative compound, or residue thereof, in the form of a diazo compound or residue thereof;

azo-coupling said diazo compound, or residue thereof, to a target compound capable of producing a detectable signal, to yield an azo-coupled complex;

quantitating and/or detecting said signal, to yield a quantitation and/or detection result; and determining from said quantitation and/or detection result the identity and/or concentration of said nitroderivative compound, or residue thereof, in said sample.

19. A method of assessing in vivo nitrative stress in a subject comprising:

(a) providing a biological specimen from said subject, said specimen comprising a protein or peptide containing at least one nitroderivative amino acid residue chosen from the group consisting of nitrotyrosine, aminotyrosine, diazotyrosine and diazoaminotyrosine;

(b) converting said nitrotyrosine and/or aminotyrosine residue(s), if present in said biological specimen, to diazotyrosine and/or diazoaminotyrosine residue(s), respectively;

(c) azo-coupling said diazoaminotyrosine residue, if present, to a target compound capable of producing a detectable signal, such that an azo-coupled protein or peptide complex is provided;

(d) if said at least one nitroderivative amino acid residue comprises diazotyrosine, azo-coupling said diazotyrosine residue to a target compound capable of producing a detectable signal, such that an azo-coupled protein or peptide complex is provided;

(e) quantitating and/or detecting said signal, to yield a quantitation and/or detection result; and assessing in viva nitrative stress in said subject from the value of said quantitation and/or detection result.

20. The method of claim 19 further comprising, prior to step (b):

($a_i$) reducing said nitrotyrosine residue(s), if present in said biological specimen, to form respective aminotyrosine residue(s).

21. The method of claim 19 wherein step (f) comprises:

($f_i$) determining from said quantitation and/or detection insult in step (e) the identity and/or concentration of said at least one nitroderivative amino acid residue in said biological specimen; and ($f_{ii}$) determining from said identification and/or concentration of said at least one nitroderivative amino acid residue a level of nitrative stress in said subject.

22. The method of claim 19 further comprising:

($a_i$) isolating said protein or peptide prior to step (b), (c) or (d), or isolating said azo-coupled protein or peptide complex resulting from step (d), prior to step (e).

23. The method of claim 19 wherein, in step (e), quantitating and/or detecting said signal comprises spectral or colorimetric monitoring of an azo-coupling reaction in step (d).

24. The method of claim 23 wherein said spectral monitoring comprises mass-spectral or fluorometric monitoring of an azo-coupling reaction in step (d).

25. The method of claim 19 wherein, in step (d), the target compound comprises a synthetic molecule containing a naphthyl moiety.

26. A method of assessing in viva nitrative stress in a subject comprising:

(a) providing a biological specimen from said subject, said specimen comprising at least one protein, peptide or nucleic acid, wherein said protein or peptide contains at least one nitroderivative compound, or residue thereof derived from tyrosine, tryptophan or histidine, and said nucleic acid contains at least one nitroderivative compound derived from guanosine;

(b) optionally, reducing said nitroderivative compound, or residue thereof, to produce the reduced form of said nitroderivative compound, or residue thereof, and (c) diazotizing said nitroderivative compound, or residue thereof or reduced form thereof, to produce a diazotized protein, peptide or nucleic acid;

(d) azo-coupling said diazolized protein, peptide or nucleic acid to a target compound capable of producing a detectable signal, such that an azo-coupled protein, peptide or nucleic acid complex is produced;

(e) quantitating and/or detecting said signal, to yield a quantitation and/or detection result; and (f) assessing in vivo nitrative stress in said subject from the value of said quantitation and/or detection result.

\* \* \* \* \*